United States Patent
Filiberti et al.

(10) Patent No.: US 12,042,670 B2
(45) Date of Patent: *Jul. 23, 2024

(54) IMAGING BASED CALIBRATION SYSTEMS, DEVICES, AND METHODS

(71) Applicants: VARIAN MEDICAL SYSTEMS, INC., Palo Alto, CA (US); Siemens Healthineers International AG, Steinhausen (CH)

(72) Inventors: Reto W. Filiberti, Baar (CH); Stephen Gaudio, Mountain View, CA (US)

(73) Assignees: VARIAN MEDICAL SYSTEMS, INC., Palo Alto, CA (US); SIEMENS HEALTHINEERS INTERNATIONAL AG, Steinhausen (CH)

(*) Notice: Subject to any disclaimer, the term of this patent is extended or adjusted under 35 U.S.C. 154(b) by 91 days.

This patent is subject to a terminal disclaimer.

(21) Appl. No.: 17/708,423

(22) Filed: Mar. 30, 2022

(65) Prior Publication Data
US 2022/0219017 A1 Jul. 14, 2022

Related U.S. Application Data

(63) Continuation of application No. 16/667,472, filed on Oct. 29, 2019, now Pat. No. 11,324,970, which is a
(Continued)

(51) Int. Cl.
*A61N 5/10* (2006.01)

(52) U.S. Cl.
CPC ............. *A61N 5/1075* (2013.01); *A61N 5/10* (2013.01); *A61N 5/1037* (2013.01); *A61N 5/1042* (2013.01); *A61N 5/1045* (2013.01); *A61N 5/1047* (2013.01); *A61N 5/1048* (2013.01); *A61N 5/1049* (2013.01); *A61N 5/1064* (2013.01); *A61N 5/1065* (2013.01); *A61N 5/1067* (2013.01); *A61N 5/1069* (2013.01); *A61N 5/107* (2013.01); *A61N 5/1077* (2013.01); *A61N 5/1081* (2013.01);
(Continued)

(58) Field of Classification Search
CPC ...... A61N 5/10; A61N 5/1037; A61N 5/1042; A61N 5/1045; A61N 5/1047; A61N 5/1048; A61N 5/1049; A61N 2005/1061; A61N 5/1064; A61N 5/1065; A61N 5/1067; A61N 5/1069; A61N 5/107; A61N 5/1075; A61N 2005/1076; A61N 5/1077; A61N 5/1081
USPC .......................................................... 378/65
See application file for complete search history.

(56) References Cited

U.S. PATENT DOCUMENTS

| | | |
|---|---|---|
| 4,998,268 A | 3/1991 | Winter |
| 5,751,781 A | 5/1998 | Brown et al. |

(Continued)

OTHER PUBLICATIONS

Chelsea M. Pearson, "Influence of Patient Weight and Couch Angle on the Accuracy of a Surface Tracking System for Monitoring of Brain Stereotactic Radiosurgery," San Diego State University, Spring 2013.

(Continued)

*Primary Examiner* — Allen C. Ho
(74) *Attorney, Agent, or Firm* — Potomac Law Group, PLLC (57) ABSTRACT

Systems, devices, and methods for imaging-based calibration of radiation treatment couch position compensations.

20 Claims, 5 Drawing Sheets

Related U.S. Application Data continuation of application No. 15/410,282, filed on Jan. 19, 2017, now Pat. No. 10,507,339, which is a continuation of application No. 14/340,985, filed on Jul. 25, 2014, now Pat. No. 9,616,251.

(52) U.S. Cl.
CPC .... *A61N 5/1082* (2013.01); *A61N 2005/1054* (2013.01); *A61N 2005/1057* (2013.01); *A61N 2005/1059* (2013.01); *A61N 2005/1061* (2013.01); *A61N 2005/1074* (2013.01); *A61N 2005/1076* (2013.01)

(56) References Cited

U.S. PATENT DOCUMENTS

| | | | |
|---|---|---|---|
| 5,901,199 | A | 5/1999 | Murphy et al. |
| 5,999,587 | A | 12/1999 | Ning et al. |
| 6,405,072 | B1 | 6/2002 | Cosman |
| 6,516,046 | B1 | 2/2003 | Frohlich et al. |
| 6,535,574 | B1 * | 3/2003 | Collins ............ A61N 5/1049 378/65 |
| 6,778,850 | B1 | 8/2004 | Adler et al. |
| 6,842,502 | B2 | 1/2005 | Jaffray et al. |
| 6,865,253 | B2 | 3/2005 | Blumhofer et al. |
| 6,888,919 | B2 | 5/2005 | Graf |
| 6,914,959 | B2 | 7/2005 | Bailey et al. |
| 6,990,175 | B2 | 1/2006 | Nakashima et al. |
| 7,147,373 | B2 | 12/2006 | Cho et al. |
| 7,188,999 | B2 | 3/2007 | Mihara et al. |
| 7,207,715 | B2 | 4/2007 | Yue |
| 7,212,608 | B2 | 5/2007 | Nagamine et al. |
| 7,221,733 | B1 | 5/2007 | Takai et al. |
| 7,227,925 | B1 | 6/2007 | Mansfield et al. |
| 7,231,076 | B2 | 6/2007 | Fu et al. |
| 7,245,698 | B2 | 7/2007 | Pang et al. |
| 7,260,426 | B2 | 8/2007 | Schweikard et al. |
| 7,289,599 | B2 | 10/2007 | Seppi et al. |
| 7,302,033 | B2 | 11/2007 | Carrano et al. |
| 7,327,865 | B2 | 2/2008 | Fu et al. |
| 7,330,578 | B2 | 2/2008 | Wang et al. |
| 7,366,278 | B2 | 4/2008 | Fu et al. |
| 7,403,638 | B2 | 7/2008 | Jeung et al. |
| 7,415,095 | B2 | 8/2008 | Wofford et al. |
| 7,418,079 | B2 | 8/2008 | Schildkraut et al. |
| 7,426,318 | B2 | 9/2008 | Fu et al. |
| 7,436,928 | B2 | 10/2008 | Urano et al. |
| 7,453,976 | B1 | 11/2008 | Yin |
| 7,453,984 | B2 | 11/2008 | Chen et al. |
| 7,505,559 | B2 | 3/2009 | Kuduvalli et al. |
| 7,522,779 | B2 | 4/2009 | Fu et al. |
| 7,574,251 | B2 | 8/2009 | Lu et al. |
| 7,590,218 | B2 | 9/2009 | Scherch et al. |
| 7,603,164 | B2 | 10/2009 | Uematsu |
| 7,609,810 | B2 | 10/2009 | Yi et al. |
| 7,613,501 | B2 | 11/2009 | Scherch |
| 7,623,623 | B2 | 11/2009 | Raanes et al. |
| 7,623,679 | B2 | 11/2009 | West et al. |
| 7,656,998 | B2 | 2/2010 | Main et al. |
| 7,657,304 | B2 | 2/2010 | Mansfield et al. |
| 7,668,292 | B1 | 2/2010 | Bose et al. |
| 7,672,429 | B2 | 3/2010 | Urano et al. |
| 7,688,938 | B2 | 3/2010 | Paliwal et al. |
| 7,729,472 | B2 | 6/2010 | Scherch et al. |
| 7,773,788 | B2 | 8/2010 | Lu et al. |
| 7,804,936 | B2 | 9/2010 | Pouliot et al. |
| 7,831,073 | B2 | 11/2010 | Fu et al. |
| 7,839,972 | B2 | 11/2010 | Ruchala et al. |
| 7,844,094 | B2 | 11/2010 | Jeung et al. |
| 7,860,550 | B2 | 12/2010 | Saracen et al. |
| 7,894,649 | B2 | 2/2011 | Fu et al. |
| 7,945,021 | B2 | 5/2011 | Shapiro et al. |
| 8,007,173 | B2 | 8/2011 | Paidi et al. |
| 8,086,004 | B2 | 12/2011 | Kuduvalli et al. |
| 8,090,074 | B2 | 1/2012 | Filiberti et al. |
| 8,116,430 | B1 | 2/2012 | Shapiro et al. |
| 8,121,368 | B2 | 2/2012 | Wiersma et al. |
| 8,126,114 | B2 | 2/2012 | Naylor et al. |
| 8,160,205 | B2 | 4/2012 | Saracen et al. |
| 8,175,892 | B2 | 5/2012 | Kapoor et al. |
| 8,198,579 | B2 | 6/2012 | Jeung |
| 8,215,836 | B2 | 7/2012 | Beaumont et al. |
| 8,218,718 | B1 | 7/2012 | Van Herk et al. |
| 8,232,535 | B2 | 7/2012 | Olivera et al. |
| 8,238,518 | B2 | 8/2012 | Poludniowski et al. |
| 8,244,330 | B2 | 8/2012 | Meier et al. |
| 8,417,318 | B2 | 4/2013 | West |
| 8,488,739 | B2 | 7/2013 | Ziegler et al. |
| 8,509,383 | B2 | 8/2013 | Lu et al. |
| 8,536,547 | B2 | 9/2013 | Maurer et al. |
| 8,559,596 | B2 | 10/2013 | Thomson et al. |
| 8,655,429 | B2 | 2/2014 | Kuduvalli et al. |
| 8,670,523 | B2 | 3/2014 | Yan et al. |
| 8,730,314 | B2 | 5/2014 | Hannibal et al. |
| 8,804,901 | B2 | 8/2014 | Maurer et al. |
| 8,824,630 | B2 | 9/2014 | Maurer et al. |
| 8,849,373 | B2 | 9/2014 | Keall et al. |
| 8,849,633 | B2 | 9/2014 | Core et al. |
| 8,861,672 | B2 | 10/2014 | Maltz et al. |
| 8,917,813 | B2 | 12/2014 | Maurer, Jr. |
| 8,934,605 | B2 | 1/2015 | Maurer et al. |
| 8,948,842 | B2 | 2/2015 | Raleigh et al. |
| 8,989,349 | B2 | 3/2015 | Thomson et al. |
| 8,989,350 | B2 | 3/2015 | Shibuya et al. |
| 8,989,846 | B2 | 3/2015 | Kuduvalli et al. |
| 9,089,696 | B2 | 7/2015 | Verhaegen et al. |
| 9,108,048 | B2 | 8/2015 | Maurer et al. |
| 9,108,049 | B2 | 8/2015 | Tsukuda et al. |
| 9,149,656 | B2 | 10/2015 | Tanabe |
| 9,192,784 | B1 | 11/2015 | Ritt et al. |
| 9,192,786 | B2 | 11/2015 | Yan et al. |
| 9,211,423 | B2 | 12/2015 | Gross et al. |
| 9,216,302 | B2 | 12/2015 | Kuwahara et al. |
| 9,280,837 | B2 | 3/2016 | Grass et al. |
| 9,283,404 | B2 | 3/2016 | Raleigh et al. |
| 9,364,186 | B2 | 6/2016 | Nioutsikou |
| 9,364,687 | B2 | 6/2016 | Raleigh et al. |
| 9,427,201 | B2 | 8/2016 | West et al. |
| 9,433,802 | B2 | 9/2016 | Handa et al. |
| 9,460,823 | B2 | 10/2016 | Song et al. |
| 9,474,913 | B2 | 10/2016 | Marash |
| 9,492,125 | B2 | 11/2016 | Deutschmann |
| 9,538,976 | B2 | 1/2017 | Keall et al. |
| 9,557,158 | B2 | 1/2017 | Hofmann et al. |
| 9,616,251 | B2 | 4/2017 | Filiberti et al. |
| 9,687,200 | B2 | 6/2017 | Maurer et al. |
| 9,724,048 | B2 | 8/2017 | Handa et al. |
| 9,844,358 | B2 | 12/2017 | Wiggers et al. |
| 9,919,166 | B2 | 3/2018 | Kontaxis et al. |
| 10,124,193 | B2 | 11/2018 | Ishikawa et al. |
| 10,272,264 | B2 * | 4/2019 | Ollila ............ A61N 5/1039 |
| 10,307,615 | B2 * | 6/2019 | Ollila ............ A61N 5/1039 |
| 10,507,339 | B2 | 12/2019 | Filiberti et al. |
| 11,045,151 | B2 | 6/2021 | Jensen et al. |
| 11,324,970 | B2 * | 5/2022 | Filiberti ............ A61N 5/107 |

OTHER PUBLICATIONS

Imad Ali et al., "Evaluation of the effects of sagging shifts on isocenter accuracy and image quality of cone-beam CT from kV on-board imagers," Journal of Applied Clinical Medical Physics, vol. 10, No. 3, Summer 2009.

Etsuo Kunieda et al., "Measurement of beam-axis displacement from the isocenter during three-dimensional conformal radiosurgery with a micro-multileaf collimator," Radiotherapy and Oncology, vol. 78 (2004) pp. 45-48.

Anees Dhabaan et al., "Six degrees of freedom CBCT-based positioning for intracranial targets treated with frameless stereotactic radiosurgery," Journal of Applied Clinical Medical Physics, vol. 13, No. 6 (2012).

Daniel E. Hyer et al., "Development and implementation of an EPID-based method for localizing isocenter," Journal of Applied Clinical Medical Physics, vol. 13, No. 6 (2012).

(56) References Cited

OTHER PUBLICATIONS

Brittany Elizabeth Cochran, "The Effect of Treatment Couches on Delivered Dose During Radiotherapy Treatments," San Diego State University, Spring 2012.

John P. Mullins et al., "Systematic offset of kV and MV localization systems as a function of gantry angle," Journal of Applied Clinical Medical Physics, vol. 12, No. 1, Winter 2011, pp. 122-128.

Megan Kovacs, et al., "Six degrees of freedom robotic correction table: Integration into routine radiotherapy practice," EORTC 2012, Haifa Israel.

Jürgen Wilbert et al., "Semi-robotic 6 degree of freedom positioning for intracranial high precision radiotherapy; first phantom and clinical results," Radiation Oncology 2010, 5:42.

R.D. Wiersma et al., "Combined kV and MV imaging for real-time tracking of implanted fiducial markers," Med Phys. 35 (4), Apr. 2008.

Milos Djordjevic, "Evaluation of Geometric Accuracy and Image Quality of an On-Board Imager (OBI)," Stockholm University and Karolinska Institute, Jul. 1, 2014 (downloaded).

James Talbot, "A Patient Position Guidance System in Radiotherapy Using Augmented Reality," Department of Physics and Astronomy, University of Canterbury, Jul. 1, 2014 (downloaded).

Fang-Fang Yin et al., "The Role of In-Room kV X-Ray Imaging for Patient Setup and Target Localization" Report of AAPM Task Group 104, American Association of Physicists in Medicine, Dec. 2009.

Winnie Li et al., "Accuracy of automatic couch corrections with on-line volumetric imaging," Journal of Applied Clinical Medical Physics, vol. 10, No. 4 (2009).

Suk Lee et al., "Evaluation of mechanical accuracy for couch-based tracking system (CBTS)," Journal of Applied Clinical Medal Physics, vol. 13, No. 6 (2012).

Huaiqun Guan et al., "A positioning QA procedure for 2D/2D (kV/MV) and 3D/3D (CT/CVCT) image matching for radiotherapy patient setup," Journal of Applied Clinical Medical Physics, vol. 10, No. 4 (2009).

D. Schmidhalter et al., "Frameless stereotactic treatments on the novalis tx: clinical range of use of a 6 degrees of freedom (6DOF) couch," Journal of Radiosurgery & SBRT, 2013 Supplement 2.1, vol. 2, pp. 35-36.

Varian Medical System, "Evaluation of IsoCal Imaging Isocenter Calibration System for Varian OBI Machines," Jul. 1, 2014 (downloaded).

Warren D. D'souza et al., "An analysis of the treatment couch and control system dynamics for respiration-induced motion compensation," Med. Phys. 33 (12), Dec. 2006.

J.-P Bissonnette et al., "Quality Assurance for image-guidance radiation therapy utilizing CT-based technologies; A report of the AAPM TG-179," Med. Phys. 39(4), Apr. 2012.

S. Gao et al., "Evaluation of IsoCal Imaging Isocenter Calibration System for Varian OBI Machines," AAPM 54$^{th}$ Annual Meeting, Jul. 1, 2014 (downloaded).

Pejman Rowshanfarzad et al., "Isocenter verification for linac-based stereotactic radiation therapy: review of principles and techniques," Journal of Applied Medical Physics, vol. 12, No. 4, Fall 2011.

\* cited by examiner

IMAGING BASED CALIBRATION SYSTEMS, DEVICES, AND METHODS

FIELD

The present disclosure relates generally to radiation therapy systems, devices, and methods, and more particularly to imaging-based calibration systems, devices, and methods for accurate target positioning and localization.

BACKGROUND

In radiosurgery or radiotherapy (collectively referred to as radiation treatment) Zo very intense and precisely collimated doses of radiation are delivered to the target region in the body of a patient in order to treat or destroy lesions. Typically, the target region is comprised of a volume of tumorous tissue. Radiation treatment requires an accurate spatial localization of the targeted lesions. Stereotactic radiosurgery (SRS) is a specific type of image-based treatment, which delivers a high dose of radiation during a single session. Because a single radiosurgery dose is more damaging than multiple fractionated doses, the target area must be precisely located.

In general, radiation treatments consist of several phases. First, a precise three-dimensional (3D) map of the anatomical structures in the area of interest (head, body, etc.) is constructed using any one of (or combinations thereof) a computed tomography (CT), cone-beam computed tomography (CBCT), magnetic resonance imaging (MRI), positron emission tomography (PET), 3D rotational angiography (3DRA), or ultrasound techniques. This determines the exact coordinates of the target within the anatomical structure, namely, locates the tumor or abnormality within the body and defines its exact shape and size. Second, a motion path for the radiation beam is computed to deliver a dose distribution that the surgeon finds acceptable, taking into account a variety of medical constraints. During this phase, a team of specialists develop a treatment plan using special computer software to optimally irradiate the tumor and minimize dose to the surrounding normal tissue by designing beams of radiation to converge on the target area from different angles and planes. Third, the radiation treatment plan is executed. During this phase, the radiation dose is delivered to the patient according to the prescribed treatment plan.

The objective of radiation therapy is to accomplish tumor control while sparing the normal tissue from radiation induced complications. This, however, requires an exact knowledge of the target position (tumor position) not only at the planning stage but also the actual treatment times. Conventionally, the tumor position is determined at one single time during the treatment planning. This information may not, however, be accurate during treatment delivery due to patient setup errors, organ motion, and variations of the geometric parameters of the system.

The prevalence of target-conforming beams, as well as the movement toward hypofractionation and dynamic arc IMRT, increases the need for accurate target positioning. Image guidance provides an improvement in positioning accuracy. Image guidance involves acquiring setup images, such as kV radiographs and/or MV portal images from multiple gantry angles, or room based X-ray systems, or MV and/or kV Cone Beam CT, as well as in-room spiral CT's or MRI images to help target localization. If gantry and imager rotation about the isocenter would be completely rigid and planar, the target positions determined from images from multiple angles would be accurate. However, gantry and imager rotation about the isocenter is not rigid and planar. Instead, a gantry head sag imposed by the weight of the gantry head, as well as similar sags in the supports for the MV image panel, kV image panel, and kV source contribute to displacements of the imaging axis and the radiation beam axis from the isocenter. Therefore, a target position determined from images obtained at multiple gantry angles could be offset significantly. In order to compensate for these offsets, the deviations between the treatment beam axis and the imaging axis need to be determined for all gantry angles and the deviations corrected.

Using a treatment couch to compensate for such deviations requires a high precision treatment couch, especially for high precision treatments such as stereotactic radiosurgery and stereotactic body radiation. Treatment couches, however, have mechanical weaknesses which, if not corrected, introduce errors in the accurate positioning and localization of the target. The currently available couch compensation models that correct for mechanical weaknesses, such as load dependent deflections, of the radiation treatment couches are couch dependent, and do not correct for installation variations or readout system production variations.

SUMMARY

An object of the present invention is to provide imaging-based systems and methods for couch offset compensations which are capable of removing installation specific imperfections.

Another object of the present invention is to provide imaging-based systems and methods for positioning a treatment couch precisely to the radiation beam isocenter for all combinations of couch rotations and gantry positions.

Another object of the present invention is increasing the accuracy of couch compensation by taking into consideration not only the gantry dependent isocenter variations but also the effects of the treatment couch rotation relative to the isocenter.

Embodiments of the present disclosure provide imaging-based calibration methods for correcting target positions by combining gantry angle dependent target position information with couch rotation angle dependent couch position offset information.

Embodiments of the present disclosure further provide methods for generating gantry angle dependent target position information for different gantry angles, and generating couch rotation angle dependent couch position offset information for different couch rotation angles.

Embodiments of the present disclosure further provide methods for correcting target positions at different gantry angles and different couch positions by combining gantry angle dependent target position information with couch rotation angle dependent couch position offset information.

BRIEF DESCRIPTION OF DRAWINGS

Embodiments will be hereinafter described with reference to the accompanying drawings, which have not necessarily been drawn to scale. Where applicable, some features may not be illustrated to assist in the illustration and description of underlying features.

DETAILED DESCRIPTION

Patients undergoing radiation therapy are typically placed on a treatment platform of a radiation treatment gantry. The gantry has a radiation source that is used to generate a radiation beam that irradiates a region of interest in the patient, such as a diseased issue including a tumor or cancerous growth site. When delivering the radiation, a plurality of radiation beams may be directed to the target area of interest from several positions outside the body. The gantry can be rotated to provide the radiation beams from different positions. The point at which beam trajectories converge or intersect is generally referred to as the isocenter. The isocenter typically receives the largest radiation dose because of the cumulative radiation received from multiple radiation beams. An integral part of the radiation treatment process is the accurate positioning of the target volume/patient at the isocenter throughout the radiation treatment process. Setup images, such as kV radiographs, and/or MV portal images, or room-based X-ray system images, or MV or kV Cone Beam CT, as well as in-room spiral CTs or MRI images, can be acquired from multiple gantry angles to aid in the accurate positioning of the patient. Because of the hardware flex, the head sag imposed by the weight of the gantry head, as well as sags in the supports for the MV image panel, kV image panel, and kV source, a target position determined from images from multiple angles may be offset significantly. Therefore, an integral part of the radiation treatment process is dependent upon the calibration of the treatment beam axis and the imaging axis for all gantry angles. In the prior art systems and methods, when an offset is determined between the treatment beam and the imaging beam, the imaging systems (on a Truebeam system, for example) or the acquired images (on Clinacs and Trilogies systems, for example) are shifted to the isocenter instead of moving the treatment couch to correct for the offset.

In the disclosed embodiments, however, when a positioning offset is determined between the reference images of the target region (e.g., volume to be treated, tumor) and the images acquired during the radiation treatment session for each gantry angle, the offset can be corrected by an operator initiated automatic couch shift from the treatment console room. Thus, the offsets can be automatically transferred to treatment couch motion from the treatment console.

Using a treatment couch to compensate for these offsets requires a high precision treatment couch, especially for high precision treatments such as stereotactic radiosurgery and stereotactic body radiation. Treatment couches have a high precision readout system built into them so as to allow for small couch shifts with high accuracy. The latest generation of couches (used on the Varian Truebeam Systems, for example) also include in their readout system, software to compensate for the structural deflection of these couches caused by the elastic mechanical distortions of the supporting structure and internal components, which position deviations are not otherwise being measured by the couch readout system. These position deviations are induced by gravity loads on the couch such as the weight of the patient and its related positioning aids (breast boards, arm rests and the like). The resulting deviations are load, as well as axis position dependent. They are also depending on the construction of the couch, but not on the individual couch, or the expected manufacturing variations. These structural deflection compensation models are used for correcting the construction dependent deviations of the couch, either for a typical load (for example between 65 to 95 kg), or, for even higher accuracy, for on the actual load, which can be measured by the couch, measured externally, or inputted as a patient specific treatment parameter.

The currently available readout systems and compensation models are, however, not compensating for errors due to different installation variations, different couch dynamics, and readout system production variations. Therefore, another integral part of the radiation treatment process is the accurate couch positioning over large ranges, which in turn is dependent on the accurate determination of the couch offset values for all couch rotation angles.

Figure 1:
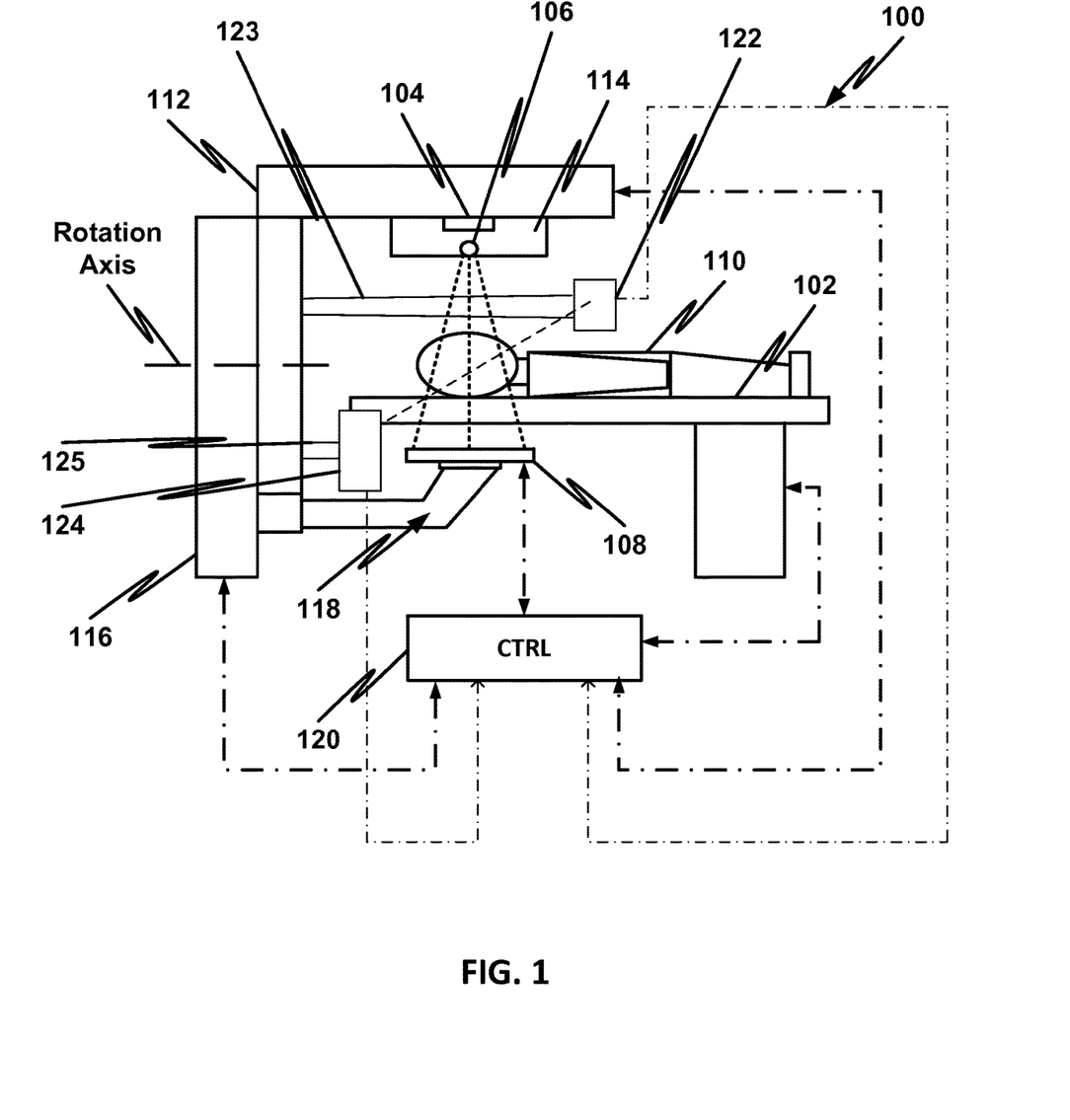
FIG. 1 illustrates a radiation treatment system according to one or more embodiments of the disclosed subject matter.

An exemplary radiation treatment system 100 that integrates radiation treatment delivery and patient setup verification is illustrated in FIG. 1. The treatment system 100 can provide radiation therapy to a patient 110 positioned on a treatment couch 102, as well as isocenter coincidence verification and couch motion offset determination prior to the commencement of the radiation treatment. The radiation therapy treatment can include photon-based radiation therapy, particle therapy, electron beam therapy, or any other type of treatment therapy.

In an embodiment, the radiation therapy treatment system 100 includes a radiation treatment device 116, such as, but not limited to, a radiotherapy or radiosurgery device, which has a gantry 112 supporting a radiation module 114 with one or more radiation sources 106 and a linear accelerator (LINAC) 104 operable to generate a beam of kilovolt (kV) or megavolt (MV) X-ray radiation. The gantry 112 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the radiation module 114 at various rotational and/or axial positions relative to the patient 110 may also be used.

The radiation module 114 can also include a modulation device (not shown) operable to modulate the radiation beam as well as to direct the therapeutic radiation beam toward the patient 110 and a portion thereof that is to be irradiated. The portion desired to be irradiated is referred to as the target or target region or a region of interest. The patient 110 may have one or more regions of interest that need to be irradiated. A collimation device such as a conventional 4 jaw collimator a multileaf collimator or fixed cones or applicators (not shown) may be included in the modulation device to define and adjust the size of an aperture through which the radiation beam passes from source 106 to patient 110. The collimation device can be controlled by an actuator (not shown), which can be controlled by controller 120.

In an embodiment, the radiation therapy device is a MV energy intensity modulated radiotherapy (IMRT) device. The intensity profiles in such a system are tailored to the treatment requirements of the individual patient. The IMRT fields are delivered with a multi-leaf collimator (MLC), which can be a computer-controlled mechanical beam shaping device attached to the head of the LINAC 104 and includes an assembly of metal fingers or leafs. The MLC can be made of 120 movable leafs with 0.5 cm and/or 1.0 cm leaf width, for example. For each beam direction, the optimized intensity profile is realized by sequential delivery of various subfields with optimized shapes and weights. From one subfield to the next, the leafs may move with the radiation beam on (i.e., dynamic multi-leaf collimation (DMLC)) or with the radiation beam off (i.e., segmented multi-leaf collimation (SMLC)). The device 116 can also be a tomotherapy device where intensity modulation is achieved with a binary collimator which opens and closes under computer control. As the gantry 112 continuously rotates around the patient 110, the exposure time of a small width of the beam can be adjusted with opening and closing of the binary collimator, allowing radiation to be delivered to the tumor through the most desirable directions and locations of the patient.

Alternatively, the device 116 can be a helical tomotherapy device, which includes a slip-ring rotating gantry or an intensity modulated arc therapy device (IMAT), which uses rotational cone beams of varying shapes to achieve intensity modulation instead of rotating fan beams. Indeed, any type of IMRT device can be employed as treatment device 116. For example, embodiments of the disclosed subject matter can be applied to image-guided radiation therapy (IGRT) devices. Each type of device 116 can be accompanied by a corresponding radiation plan and radiation delivery procedure.

The treatment couch 102 is positioned adjacent to the gantry 112 to place the patient 110 and the target volume within the range of operation of the X-ray source 106. The treatment couch 102 may be connected to the rotatable gantry 112 via a communications network and is capable of translating in multiple planes and angulations for positioning and repositioning the patient 110 and the target volume.

The treatment couch 102 can have three or more degrees of freedom. The treatment couch 102 can be coupled to an automated patient positioning system capable of manipulating the patient with three or more degrees of freedom (e.g., three orthogonal translations plus one or more rotations). In embodiments, the treatment couch 102 can have six (6) degrees of freedom (i.e., 6 DoF couch), namely, it can move in the vertical, lateral, longitudinal, rotation (yaw), roll, and pitch directions (x, y, z, $\theta_1$, $\theta_2$, $\theta_3$). In such a case, the automated patient positioning system is capable of manipulating the patient with six degrees of freedom (e.g., three orthogonal translations and three rotations). In other embodiments, the treatment couch 102 can have four (4) degrees of freedom (i.e., 4 DoF couch), namely, it can move in the vertical, lateral, longitudinal directions and have one rotation direction (x, y, z, $\theta_1$). In such a case, the automated patient positioning system is capable of manipulating the patient with four degrees of freedom (e.g., three orthogonal translations and one rotation).

The treatment couch 102 includes a built-in high precision readout system to allow for small couch shifts with high accuracy. The readout system can be a digital readout system and can include one or more couch angle encoding potentiometers, or other position and angle sensors, including, but not limited to, optical or magnetic rotary (angle) or linear encoders. These position and angle sensors and potentiometers, supply input signals regarding the positions/movement/angle of the treatment couch 102 to the digital readout system on the console. The encoders include serial interface technology to provide secure data transmission of absolute positioning values. The encoders can be fitted with the treatment couch 102 and can be integrated with the radiation treatment system. For example, one or more encoders can be used in the motor packages that operate in conjunction with the couch's vertical/downwards/lateral movement. Additional encoders are used for the pitch and roll motion axis of the treatment couch 102. Each axis of movement can also have secondary, 'fail-safe' encoders, which during system operation constantly check against the primary 'master' encoders for successful non-stop system operation.

The readout system also includes software that integrates treatment couch travel and positioning with beam delivery, as well as software to compensate for the structural deflection of the couch 102 caused by the elastic mechanical distortions of the supporting structure and internal components, which position deviations are not otherwise being measured by the couch readout system. These position deviations are induced by gravity loads on the couch such as the weight of the patient and its related positioning aids (breast boards, arm rests and the like). The resulting deviations are load, as well as axis position dependent. They are also dependent on the construction of the couch 102 and the expected couch manufacturing variations. These structural deflection compensation models are used for correcting the construction dependent deviations of the couch, either for a typical load (for example between 65 to 95 kg), or, for even higher accuracy, for the actual load, which can be measured by a measuring device integrated with the couch 102, measured externally, or inputted as a patient specific treatment parameter. The treatment couch 102 can be positioned along a vertical axis at a height which is at one of the height of the isocenter, above the isocenter, or below the isocenter.

Device 116 can also include a holding structure 118, which could be a robotic, servo controlled arm holding an imager 108 for acquiring digital images. The imager 108 can include a megavoltage (MV) electronic portal imaging device (EPID). The imaging device 108 can be placed at different locations, and can generate immediate 2-D digital information. By acquiring a plurality of MV images at different gantry angles, a MV-Cone beam CT image can be generated and be used for positioning.

The system 100 can further include a (kV) X-ray imaging system including an X-ray source 122 and a corresponding X-ray detector/imager 124, both installed on the gantry 112 using arms 123, 125 to allow for patient setup and target localization. The kV imaging system not only allows 2D patient setup, but it can also acquire cone beam CT (CBCT) for 3D patient setup. In general, this is done by generating a plurality of kV images using the kV imaging system right before the start of each radiation treatment session and comparing the acquired images with corresponding patient reference images previously generated during the treatment planning phase. The detected differences between the online images (either 2D-kV image or 3D-CBCT image) and the patient reference images (either 2D-DRR images or 3D-planning CT images) can be automatically transferred to treatment couch motion from the treatment console including controller 120, as described in detail herein.

Arms 123, 125 could be electronically stabilized, robotic arms (electronic servo arms, for example) that hold the X-ray source 122 and the imager 124 in a stable configuration relative to the gantry 112. The arms 123 and 125 can have parked, partially extended, and extended positions. These positions can be programmed into the controller 120, and the arm positions can be extended or retracted remotely. Each of the arms 123, 125 can be controlled individually, as a pair, or together with arm 118.

The kV X-ray imaging system can be mounted on the gantry 112 orthogonal to the MV X-ray imaging system 108, while sharing the same isocenter of the radiation treatment source 106. The X-ray source 122 could be an X-ray tube, and the X-ray detector/imager 124 could be a high-performance flat-panel imager, for example. Both the X-ray source 122 and the X-ray imager 124 could be moved laterally and longitudinally relative to the treatment beam, and be rotated through 360 degrees around the patient together with the X-ray radiation treatment source 106 and MV X-ray imager 108 in both clockwise and counterclockwise directions. The movement of the X-ray source 122 and X-ray imager 124 could also be controlled by the controller 120.

Controller 120 can include a computer with typical hardware such as a processor, and an operating system for running various software programs and/or communication applications. The computer can include software programs that operate to communicate with the radiation therapy device 116, which software programs are operable to receive data from external software programs and hardware. The computer can also include any suitable input/output devices adapted to be accessed by medical personnel, as well as input/output (I/O) interfaces, storage devices, memory, keyboard, mouse, monitor, printers, scanner, etc. The computer can also be networked with other computers and radiation therapy systems. Both the radiation therapy device 116 and the controller 120 can communicate with a network as well as a database and servers. The controller 120 can be configured to transfer medical image related data between different pieces of medical equipment.

The system 100 can also include a plurality of modules containing programmed instructions (e.g., as part of controller 120, or as separate modules within system 100, or integrated into other components of system 100), which instructions cause system 100 to perform different functions related to radiation therapy/surgery, as discussed herein, when executed. The system 100 can, for example, include a treatment delivery module operable to instruct the radiation therapy device 116 to deliver a radiation plan with or without the patient 110 in place; an image processing module operable to receive images from the kV X-ray imager 124 as well as the MV X-ray imager 108; a comparison module operable to compare the acquired kV and MV X-ray images with corresponding reference images and determine shifts between the kV imaging axis, the MV imaging axis, and the radiation beam axis; an isocenter calibration module operable to align the kV/MV imaging isocenters to the treatment isocenter based on the comparison; a calculation module operable to determine the amount of alignment needed (i.e., isocenter shift/offset determination); a couch offset determination module operable to determine couch offset information relative to the isocenter at each couch rotation angle; a calibration module operable to combine the gantry angle dependent isocenter offset information with the couch offset information, generate gantry angle dependent couch offset information, and generate correction information for all treatment couch axis based on the gantry angle dependent couch offset information. The modules can be written in C or C++ programming languages, for example. Computer program code for carrying out operations as described herein may also be written in other programming languages.

Figure 2:
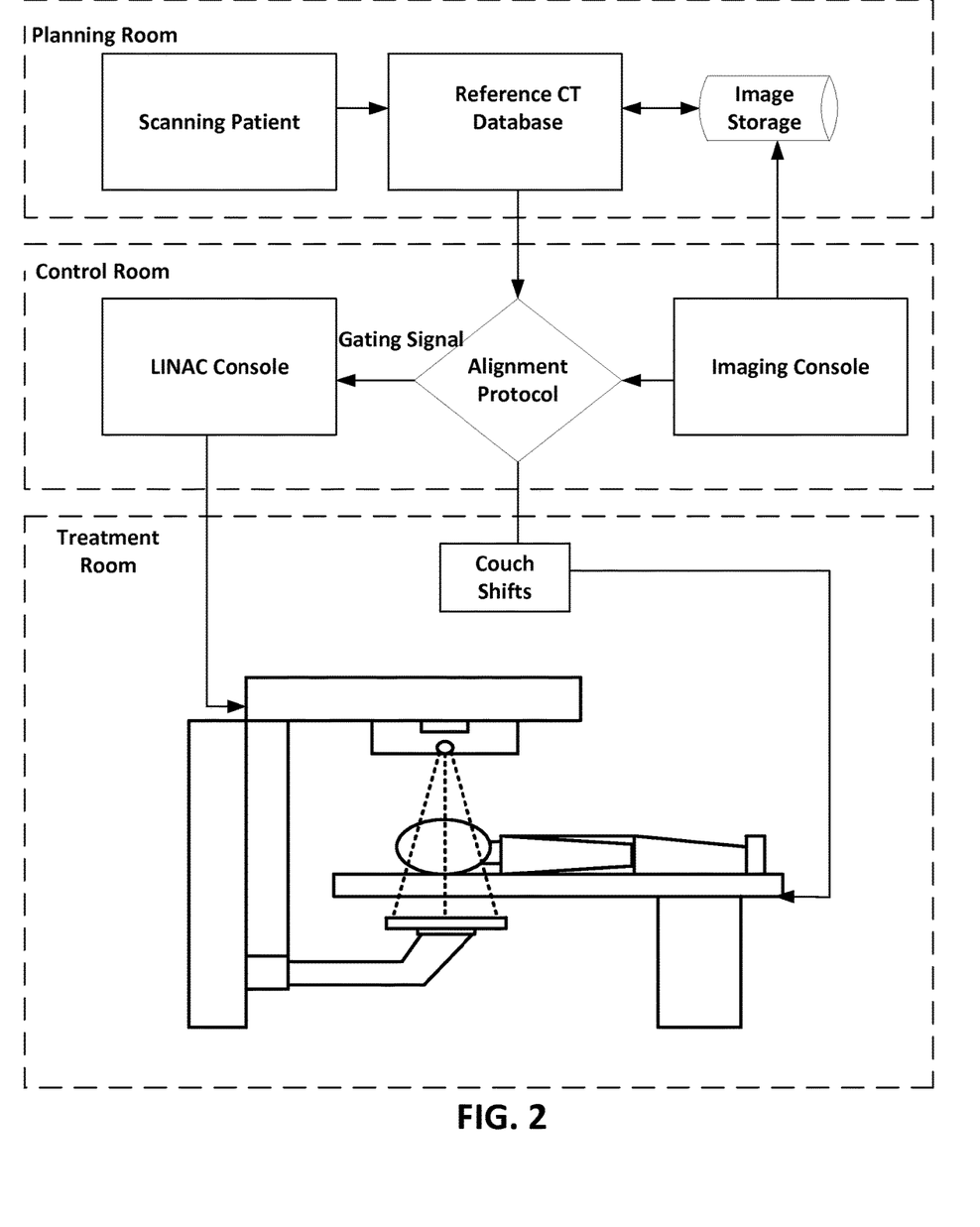
FIG. 2 illustrates a process flow according to one or more embodiments of the disclosed subject matter.

The system 100 including the kV imaging system 122, 124 and the MV X-ray imager 108 integrated with the radiation treatment device 116 allows all image guidance activities, such as, image acquisition, image registration/interpretation, and patient correction to occur remotely. Remote couch motion allows for all axis of the treatment couch 102 to be adjusted remotely based on the information generated by the system. System 100 also allows capture of all data needed for the image acquisition (i.e., gantry angle, reference images, imager positions, type of image to be acquired (radiograph or CBCT), etc.). All data can be transferred between different computers and radiation therapy systems using DICOM RT (RT Plan, RT Structure Set, RT Image Objects) as shown in FIG. 2. Although, the illustrative embodiment includes a kV imaging system which is integral with the gantry 112, the kV imaging system can be a separate imaging system, such as a room based imaging system.

FIG. 2 illustrates a clinical workflow (process) using X-ray imaging for patient/target localization. The radiation treatment includes acquiring a treatment planning scan of a patient in the treatment position in the treatment planning room. The combination of the resulting CT images and associated contours defines a reference CT dataset. The reference CT dataset is imported to the workstation in the control room. The patient is then positioned on the treatment couch 102 in the treatment room. Localization imaging, such as, but not limited to, CBCT imaging, is then performed, using the X-ray imaging system. After scanning, the localization images are registered to the reference CT images to determine the patient and tumor position. The alignment/fusion of these two datasets may be performed using different algorithms. The result of the alignment is the determination of the required adjustments in the patient/tumor positions. Once the required adjustments are determined, the necessary translations/rotations are automatically sent to the treatment device and the treatment couch 102 is automatically moved. The registration information and the fusion graphic can be stored in a database.

Calibration Procedure

Figure 3:
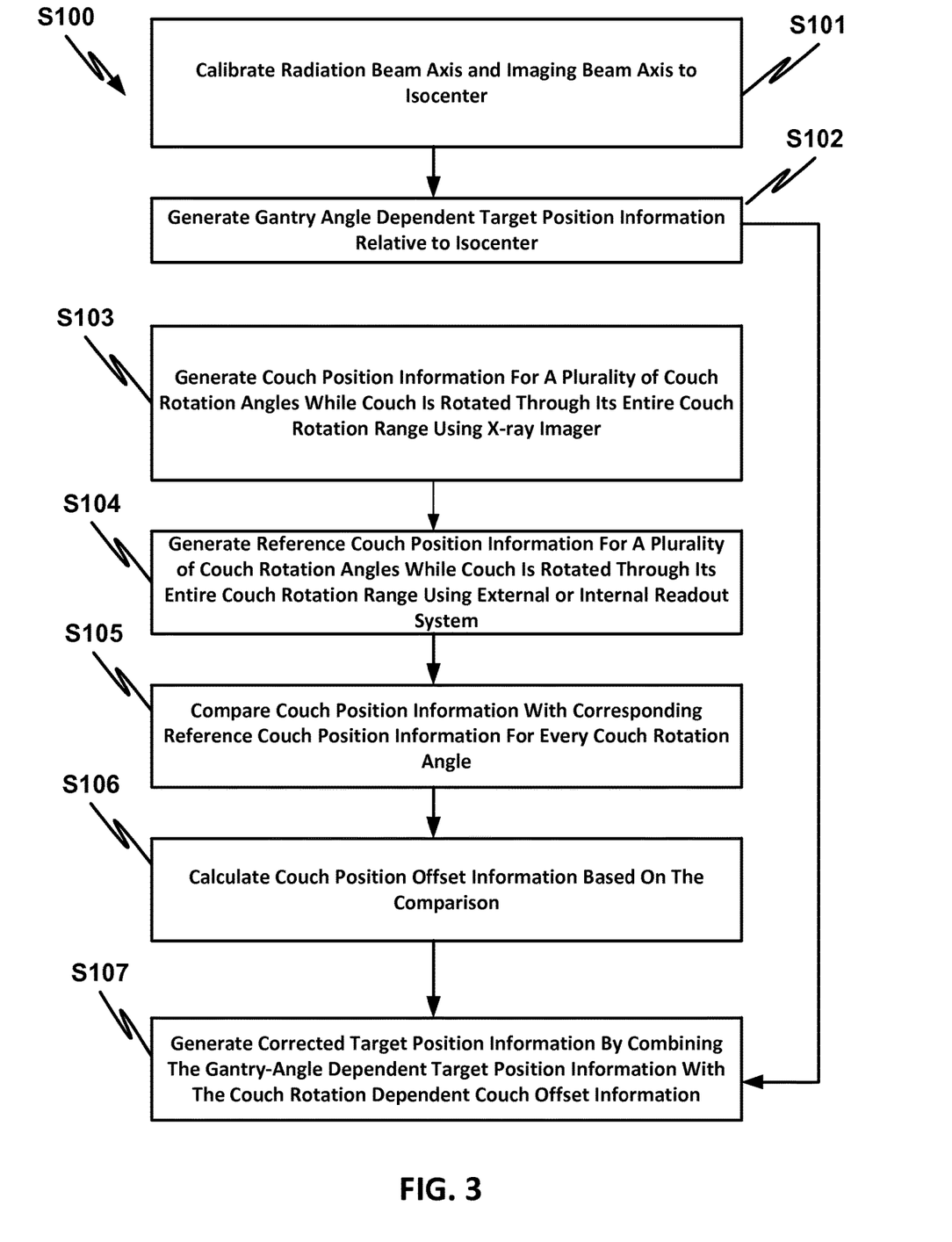
FIG. 3 illustrates a flow diagram of an imaging-based calibration process according to one or more embodiments of the disclosed subject matter.

In operation, prior to radiation treatment of the patient 110, as part of an implemented quality assurance (QA) protocol, the controller 120 initiates an imaging-based calibration process S100, shown in FIG. 3, that compensates for gantry angle dependent isocenter deviations as well as couch motion offsets. The first step S101 in the calibration process S100 includes a process by which the MV treatment beam axis, the MV imaging axis, and the kV imaging axis are calibrated to the isocenter. This process S101 can include, but is not limited to, the automated IsoCal™ calibration method (Varian Medical Systems, Palo Alto, CA), incorporated herein by reference in its entirety. The IsoCal calibration method includes a combination of hardware (calibration phantom/device, collimator plate) and software to automatically align the imaging isocenters to the treatment isocenter using the calibration phantom and associated software.

In Step S101, a calibration device, such as a calibration phantom, of known geometry, and a collimator or transmission plate with a radio-oblique pin are positioned on the treatment couch 102 in a secured known fixed position. The calibration device (phantom) can be, but is not limited to, an acrylic cube with engravings to indicate the centers of each surface to aid aligning the calibration cube at an isocenter. Inside the cube, at its center, a small (2 mm range) tungsten-carbide BB sphere can be positioned. One or more additional markers including visible and IR reflective markers can be positioned on different sides and locations of the cube. These markers can be made of materials that allow them to be distinguishable from the rest of the image. Any other available calibration devices, such as, but not limited to, a 6D QA phantom, appropriate for kV imaging, MV imaging, and treatment and coordinate coincidence verifications may be used. Other calibration devices, such as those appropriate for isocenter determination, positioning of the patient at the treatment device using various kinds of positioning and monitoring systems (kV, MV, CT, CCBCT, DTS, and optical surface monitoring system), testing and validating the measurement accuracy of two-dimensional (2D) and three-dimensional (3D) image measurement devices and tools installed on the medical imaging system 100, as well as verification of the measurement accuracy of digital image viewing stations that include diagnostic, clinical review, internet browser and teleradiology network of transferred medical diagnostic image systems can also be used. The calibration device (phantom) can be a three-dimensional phantom assembly that can be used to independently verify the phantom or isocenter position by the use of various positioning systems available on the treatment device, and is able to quantitatively determine the shift between the different isocenter/imaging centers used. The calibration device is also configured to facilitate image-based positioning of the calibration device using kV, MV, and optical surface monitoring.

Next, the automated isocenter calibration system and method involves aligning the imaging isocenters (kV/MV imaging axis) to the treatment isocenter (treatment beam axis) by imaging the calibration phantom of known geometry at four (4) collimator positions (the collimator positions can have more or less than 4 collimator positions) for example, to find its axis, and then taking a plurality of kV X-ray and MV X-ray projection images of the calibration phantom with the kV source/imager system 122/124, and the MV source/imager system 106/108, respectively, at a plurality of gantry angles during a 360 degree rotation of the gantry 112 around the calibration phantom. In an exemplary embodiment, the gantry 112 can be rotated at an increment of 1 degrees between the acquisition of each image for a complete 360 degree rotation, for example, where at zero (0) degrees, the gantry is pointing to the floor, and at 180° it is pointing to the ceiling. The gantry 112, however, can be rotated at different increments of gantry angles. The gantry could also be rotated for less than 360 degrees. Alternatively, the gantry 112 can be rotated at an increment of 1 degrees between the acquisition of each image for a complete 360 degree rotation, for example, where the starting position of the gantry is at 180 degrees. The gantry 112, however, can be rotated at different increments of gantry angles. The gantry could also be rotated for less than 360 degrees.

From the plurality of kV and MV projections so obtained, an algorithm, such as, but not limited to, IsoCal™ calibration algorithm can be applied to determine the gantry 112 rotational axis and the positions of the three isocenters on it (kV/MV imager isocenter and MV radiation treatment beam isocenter). The isocenters are next projected onto the imagers 108, 125 to determine correction shift vectors. The correction shift vectors $\Delta_{in}$ (beam isocenter offsets) are 2D vectors (x, y) which indicate the lateral and longitudinal offsets, respectively, between the treatment beam isocenter and the kV/MV image centers. The controller 120 can also generate a correction file including the correction shift vectors $\Delta_{in}$ indicating the deviations of the actual treatment beam at each gantry angle ($\theta_{gn}$). These gantry-angle dependent deviations ($\Delta_{in}$) can be later applied to the MV/kV system to correct for offsets in the positions of the imaging axis. Correcting the offsets in the positions of the imaging axis can be done by applying the gantry dependent position offsets ($\Delta_{in}$) to the imaging system (imager arm or X-ray tube arm) or by shifting the acquired images by the amount of the image system offset ($\Delta_{in}$). Once the offsets are corrected, the exact position of the calibration phantom in relation to the isocenter can be determined for each gantry angle in the range $\theta_{g0}$-$\theta_{gn}$, where n could be, but is not limited to, 360. By knowing the exact position of the calibration phantom relative to the isocenter at each gantry angle, in step S102, the position of a target relative to the isocenter can be determined for each gantry angle, and thus, gantry-angle dependent target position information ($T_n$) can be generated. The beam isocenter offset values ($\Delta_{in}$) together with the corresponding gantry angles ($\theta_{gn}$) and respective target ($T_n$), and corresponding couch ($C_n$) locations, relative to the isocenter can be recorded in a tabular format, as a correction file, as shown in Table 1 below, and saved in a memory of the controller 120, for example.

TABLE 1

| Gantry Angle $\theta_{gn}$ (degrees) | $\theta_{g0}$ | $\theta_{g1}$ | $\theta_{g2}$ | $\theta_{g3}$ | $\theta_{g4}$ | . . . . . . | $\theta_{gn}$ |
|---|---|---|---|---|---|---|---|
| Beam Isocenter Offset Information $\Delta_{in}$ | $\Delta_{i0}$ | $\Delta_{i1}$ | $\Delta_{i2}$ | $\Delta_{i3}$ | $\Delta_{i4}$ | . . . . . . | $\Delta_{in}$ |
| Target Position $T_n$ relative to the isocenter | $T_0$ | $T_1$ | $T_2$ | $T_3$ | $T_4$ | . . . . . . | $T_n$ |
| Couch Location relative to isocenter $C_n$ (x, y, z, $\theta_1$, $\theta_2$, $\theta_3$) | $C_0$ | $C_1$ | $C_2$ | $C_3$ | $C_4$ | . . . . . . | $C_n$ |

Couch Rotation-Angle Dependent Couch Offset Calculation

In step S103, the couch rotation angle dependent couch position offset information is generated. During this step, a plurality of megavoltage MV X-ray images of the calibration phantom are captured by the MV imager 108 using MV X-rays from source 106, while the couch 102 is rotated over its entire couch rotation range. The couch rotation range includes 360 degrees, for example. However, in alternative embodiments, the couch rotation range can include less than 360 degrees. To capture the MV X-ray images, the gantry 112 is positioned at a first position, at 0 degree angle (MV source at the 12 o'clock position radiating downwards, i.e., at zero degrees the gantry is pointing to the floor, and at 180° it is pointing to the ceiling) for example, and the treatment couch 102 is rotated in a clockwise direction from a first starting position to its maximum rotation angle (maximum rotation angle for the treatment couch could be, but is not limited to, 100 degrees), while images are acquired at 1 degree rotation angle increments. Thus, for each degree of couch rotation, a MV X-ray image of the calibration phantom is generated. Then, the treatment couch 102 is rotated to its maximum rotation angle in a second, counterclockwise direction, acquiring a MV X-ray image at each 1 degree rotation increment. In the exemplary embodiment, the rotation of the treatment couch 102 is in 1 degree increments. However, the treatment couch 102 can be rotated at any other degree increments, such as, but not limited to, 1.5 or 2 degree increments.

Next, the gantry 112 is positioned in a second position, such as between 5-60 degrees or between 30 and 60 degrees, (between the 1 o'clock and the 2 o'clock positions) for example, and the treatment couch 102 is rotated to its maximum rotation angle in the clockwise direction while acquiring MV X-ray images of the calibration phantom at a plurality of couch rotation angles. The treatment couch 102 can be rotated in 1 degree increments, and at each couch rotation angle a corresponding X-ray image can be acquired. The treatment couch is then rotated to its maximum rotation angle in a counterclockwise direction while acquiring MV X-ray images of the phantom at a plurality of couch rotation angles. The treatment couch 102 again can be rotated 1 degrees at a time and a corresponding X-ray image generated. In the exemplary embodiment, the rotation of the treatment couch 102 is in 1 degree increments. However, the treatment couch 102 can be rotated at any other degree increments, such as, but not limited to, 1.5 or 2 degree increments.

Next, the gantry 112 is positioned in a third position, such as between 300 and 355 or between 320-340 degrees (between the 10 o'clock and the 11 o'clock positions), for example, and the treatment couch 102 is rotated to its maximum rotation angle in the clockwise direction while acquiring MV X-ray images of the calibration phantom at a plurality of couch rotation angles. The treatment couch 102 can be rotated in 1 degree increments, and at each couch rotation angle a corresponding X-ray image can be acquired. The treatment couch is then rotated to its maximum rotation angle in a counterclockwise direction while acquiring MV X-ray images of the calibration phantom at a plurality of couch rotation angles. The treatment couch 102 again can be rotated 1 degree at a time and a corresponding X-ray image generated. In the exemplary embodiment, the rotation of the treatment couch 102 is in 1 degree increments. However, the treatment couch 102 can be rotated at any other degree increments, such as, but not limited to, 1.5 or 2 degree increments.

In the illustrative embodiment, the gantry 112 is first positioned at 0 degrees, then at between 30-60 degrees, then at between 300-330 degrees, respectively, prior to acquiring of the MV X-ray images. However, any other gantry angle positions and/or combination of gantry angles are contemplated. Therefore, the gantry may start at the 0 degree position followed by the 300-330 degree position followed by the 30-60 degree position, or any other gantry angle combination. In alternative embodiments, the gantry may be positioned only at two different locations. In yet other embodiments, the gantry may be positioned at more than three different locations.

In an alternative embodiment, the initial gantry position is at 180 degrees (i.e., radiation is pointing to the ceiling), then the gantry 112 is rotated through 360 degrees by first positioning the gantry at 180 degrees, then at between 210-220 degrees or between 185-240 degrees, then at between 140-160 degrees or between 120-175 degrees, respectively, prior to acquiring of the MV X-ray images. However, any other gantry angle positions and/or combination of gantry angles are contemplated.

Each of the MV X-ray images so generated includes the markers embedded in the calibration phantom. In order to determine a position of the calibration phantom from an X-ray image, first the positions of the markers in the X-ray image is determined, then a one-to-one correspondence algorithm applied, whereby a correspondence is detected between the projections of each marker in the X-ray image and the markers themselves in the phantom. The positions of the markers in an X-ray image can be determined using a conversion algorithm by which the image frame is converted to a binary image by thresholding. The binary image can then be analyzed by the controller 120 and the positions of the markers in the generated image determined. Other known techniques could also be used to determine the positions of the markers in the generated X-ray image. Once the positions of the markers in the X-ay image are determined, the controller 120 can form a one-to-one correspondence between the projections of each marker in the X-ray image and the markers themselves in the phantom. This can be done by determining a possible orientation of the phantom that could produce the arrangement of the markers in the X-ray image. The possible orientation of the phantom translates into possible couch orientations/positions that would support such a phantom orientation. Various other available algorithms could be used for such determination. Once a match has been found, the estimated position of the calibration phantom is determined to be the position of the calibration phantom at the corresponding couch rotation angle. By applying this image processing technique for all MV X-ray images obtained, the position of the phantom at each couch rotation angle can be determined. The MV X-ray images so generated therefore contain information about the positions of the calibration phantom and corresponding treatment couch positions for all couch rotation angles.

The plurality of couch positions for all couch rotation angles obtained in step S103 are next compared to corresponding reference couch positions to determine the couch position offsets for each couch rotation angle. The reference couch position information can be obtained in S104 using the digital readout system which is internal to the radiation treatment device (LINAC), or using an external readout system, which is external to the radiation treatment device, but it is integrated with its operation.

When the internal digital readout system is used, the reference couch positions are generated during the movement of the couch 102 as described above in S103. During the movement of the treatment couch 102 through the couch rotation angles, the position of the treatment couch for each couch rotation angle is measured using the potentiometers and/or encoders integrated with the internal readout system. From this, the readout system can compute couch position information for each couch rotation angle. From this information, in S105, reference couch position information ($C_{rn}$) (x', y', z', $\theta'_1$, $\theta'_2$, $\theta'_3$) for all couch rotation angles ($\theta c_n$) can be generated.

In an alternative embodiment, an external readout system can be used to generate the plurality of reference couch locations. Such a system could be, but is not limited to, the ExacTrac™ (Brainlab Germany) or AlignRT™ (VisionRT Ltd, London UK) imaging and control systems. These imaging and control systems use real-time infrared (IR) and X-ray (ExacTrac™), or visible light (AlignRT™) to measure the positions of the calibration phantom (its surface), compare the measured positions with the detected positions, and determine position offsets between the two.

In operation, two (Brainlab) or three (VisionRT) camera systems, mounted from the ceiling of the treatment room (e.g., two room based X-ray Imaging Chains), record the positions of IR reflective markers on the calibration phantom surface, or the positions of the X-ray visible markers on the phantom. From these images, the readout system can compute 3D position information of the calibration phantom. When the calibration phantom is moved to different locations by rotating the treatment couch 102, one degree at the time, through its entire couch rotation range (i.e., during S103), the readout system can compute 3D phantom position information for each couch rotation angle. From this information, in S105, reference couch position information ($C_{rn}$) (x', y', z', $\theta'_1$, $\theta'_2$, $\theta'_3$) for all couch rotation angles ($\theta c_n$) can be generated.

The readout systems (internal and external) also include image registration algorithms to compare, for each couch rotation angle ($\theta c_u$), the phantom/couch position information obtained using the X-ray image (S103) with a corresponding reference phantom/couch position information obtained using the potentiometers and/or encoders (internal readout system), or the IR or visible camera system (external readout system). The difference between the determined (i.e., measured) ($C_{mn}$) and reference ($C_{rn}$) couch positions for each couch rotation angle ($\Theta c_n$) can be calculated in S106. The calculated couch position offsets (couch position offset values $\Delta_{cn}$) represent the longitudinal, lateral, vertical, and rotational displacements, respectively, between the determined $C_{mn}$ (x, y, z, $\theta_1$, $\theta_2$, $\theta_3$) and the reference ($C_{rn}$) (x', y', z', $\theta'_1$, $\theta'_2$, $\theta'_3$) couch positions for every couch rotation angle ($\Theta c_n$), where $\Delta_{cn}=(C_{mn})-(C_{rn})$; $\Delta_x=$x-x'; $\Delta_y=$y-y'; $\Delta_z=$z-z'; $\Delta_{\theta 1}=\theta_1-\theta'_1$; $\Delta_{\theta 2}=\theta_2-\theta'_2$; $\theta_3=\theta_3-\theta'_3$. These offset values $\Delta_{cn}$ can be stored in a tabular format, as shown in Table 2 and saved in a memory of the controller 120, for example.

TABLE 2

| Couch Rotation Angle $\Theta c_n$ (degrees) | $\Theta c_0$ | $\Theta c_1$ | $\Theta c_2$ | $\Theta c_3$ | $\Theta c_4$ | ...... | $\Theta c_n$ |
|---|---|---|---|---|---|---|---|
| Measured Couch location $C_{mn}$ (x, y, z, $\theta_1$, $\theta_2$, $\theta_3$) | $C_{m0}$ | $C_{m1}$ | $C_{m2}$ | $C_{m3}$ | $C_{m4}$ | ...... | $C_{mn}$ |
| Reference Couch location $C_{rn}$ (x', y', z', $\theta'_1$, $\theta'_2$, $\theta'_3$) | $C_{r0}$ | $C_{r1}$ | $C_{r2}$ | $C_{r3}$ | $C_{r4}$ | ...... | $C_{rn}$ |
| Couch location offset $\Delta_{cn}$ ($\Delta_x$, $\Delta_y$, $\Delta_z$, $\Delta_{\theta 1}$, $\Delta_{\theta 2}$, $\Delta_{\theta 3}$) | $\Delta_{c0}$ | $\Delta_{c1}$ | $\Delta_{c2}$ | $\Delta_{c3}$ | $\Delta_{c4}$ | ...... | $\Delta_{cn}$ |

In step S107, the calibration process S100 generates corrected target position ($T'_n$) information by combining the gantry-angle dependent target position information (Table 1) with the couch rotation dependent couch offset information (Table 2), as shown in Table 3. Table 3 can also be saved in a memory of the controller 120, for example.

By combining the information obtained from the gantry-angle dependent isocenter calibration process S101-S102 shown in Table 1, with the couch location offset information obtained from the couch angle-dependent couch position offset calculation process S103-S106 shown in Table 2, an accurate target position information ($T'_n$) for each gantry angle/couch angle combination can be obtained, as shown in Table 3. The accurate target position information ($T'_n$) represents the positions of the target after the target has been repositioned from the original target position ($T_n$) by an amount corresponding to the couch offset values $\Delta_{cn}$ for respective gantry angles $\Theta_{gn}$ and couch rotation angles $\Theta c_n$.

TABLE 3

| Gantry Angle $\Theta_{gn}$ (degrees) | $\Theta_{g0}$ | $\Theta_{g1}$ | $\Theta_{g2}$ | $\Theta_{g3}$ | $\Theta_{g4}$ | ...... | $\Theta_{gn}$ |
|---|---|---|---|---|---|---|---|
| Couch Rotation Angle $\Theta c_n$ (degrees) | $\Theta c_0$ | $\Theta c_1$ | $\Theta c_2$ | $\Theta c_3$ | $\Theta c_4$ | ...... | $\Theta c_n$ |
| Couch location $C_n$ (x, y, z, $\theta_1$, $\theta_2$, $\theta_3$) | $C_0$ | $C_1$ | $C_2$ | $C_3$ | $C_4$ | ...... | $C_n$ |
| Couch location offset $\Delta_{cn}$ ($\Delta_x$, $\Delta_y$, $\Delta_z$, $\Delta_{\theta 1}$, $\Delta_{\theta 2}$, $\Delta_{\theta 3}$) | $\Delta_{c0}$ | $\Delta_{c1}$ | $\Delta_{c2}$ | $\Delta_{c3}$ | $\Delta_{c4}$ | ...... | $\Delta_{cn}$ |
| Accurate Target position information $T'_n$ relative to the isocenter | $T'_0$ | $T'_1$ | $T'_2$ | $T'_3$ | $T'_4$ | ...... | $T'_n$ |

By combining the accurate isocenter calibration of the MV treatment beam (Table 1) and the couch compensation with the couch offset (Table 2), the treatment couch 102 and thus, the target, can be accurately positioned to the beam isocenter for every combination of couch 102 rotation and gantry 112 rotation (Table 3). Various interpolation methods, such as, but not limited to, linear interpolation, cubic interpolation, Hermite interpolation, trilinear interpolation, linear regression, curve fit through arbitrary points, as well as nearest neighbour weighted interpolation methods can be used to obtain intermediate values for these parameters, including the couch location offset values $\Delta_{cn}$.

In alternative embodiments, process S100 can be repeated for different couch loads (i.e., different weights added to the treatment couch 102) to also calibrate for the load offsets. In such embodiments, for each treatment iteration, weights can be added to the treatment couch 102 to simulate different sized patients, and the process steps S103-S104 repeated to generate determined (i.e., measured) ($C_{mn}$) and reference couch positions ($C_{rn}$). The difference between the determined (i.e., measured) ($C_{mn}$) and reference ($C_{rn}$) couch positions for each couch rotation angle ($\Theta c_n$) can then be calculated in S106 by comparing the measured and reference couch positions for each couch rotation angle and for each load. The calculated couch position offsets (couch position offset values $\Delta'_n$) represent the longitudinal, lateral, vertical, and rotational displacements, respectively, between the determined $C_{mn}$ (x, y, z, $\theta_1$, $\theta_2$, $\theta_3$) and the reference ($C_m$) y', z', $\theta'_1$, $\theta'_2$, $\theta'_3$) couch positions for every couch rotation angle ($\Theta c_n$) and respective couch load;

where $\Delta'_{cn}=(C_{mn})-(C_m)$; $\Delta'_x=$x-x'; $\Delta'_y=$y-y'; $\Delta'_z=$z-z'; $\Delta'_{\theta 1}=\theta_1-\theta'_1$; $\Delta'_{\theta 2}=\theta_2-\theta'_2$; $\Delta'_3=\theta_3-\theta'_3$. These offset values $\Delta'_{cn}$ can be stored in a tabular format, as shown in Table 4, and saved in a memory of the controller 120, for example.

TABLE 4

| Load (lbs/kg) | $L_0$ | $L_1$ | $L_2$ | $L_3$ | $L_4$ | ...... | $L_n$ |
|---|---|---|---|---|---|---|---|
| Couch location offset $\Delta'_{cn}$ ($\Delta'_x$, $\Delta'_y$, $\Delta'_z$, $\Delta'_{\theta 1}$, $\Delta'_{\theta 2}$, $\Delta'_{\theta 3}$) | $\Delta'_{c0}$ | $\Delta'_{c1}$ | $\Delta'_{c2}$ | $\Delta'_{c3}$ | $\Delta'_{c4}$ | ...... | $\Delta'_{cn}$ |

In yet other embodiments, additional offsets for collimator jaw, MLC, cones as well as applicator imperfections could also be included.

Figure 4:
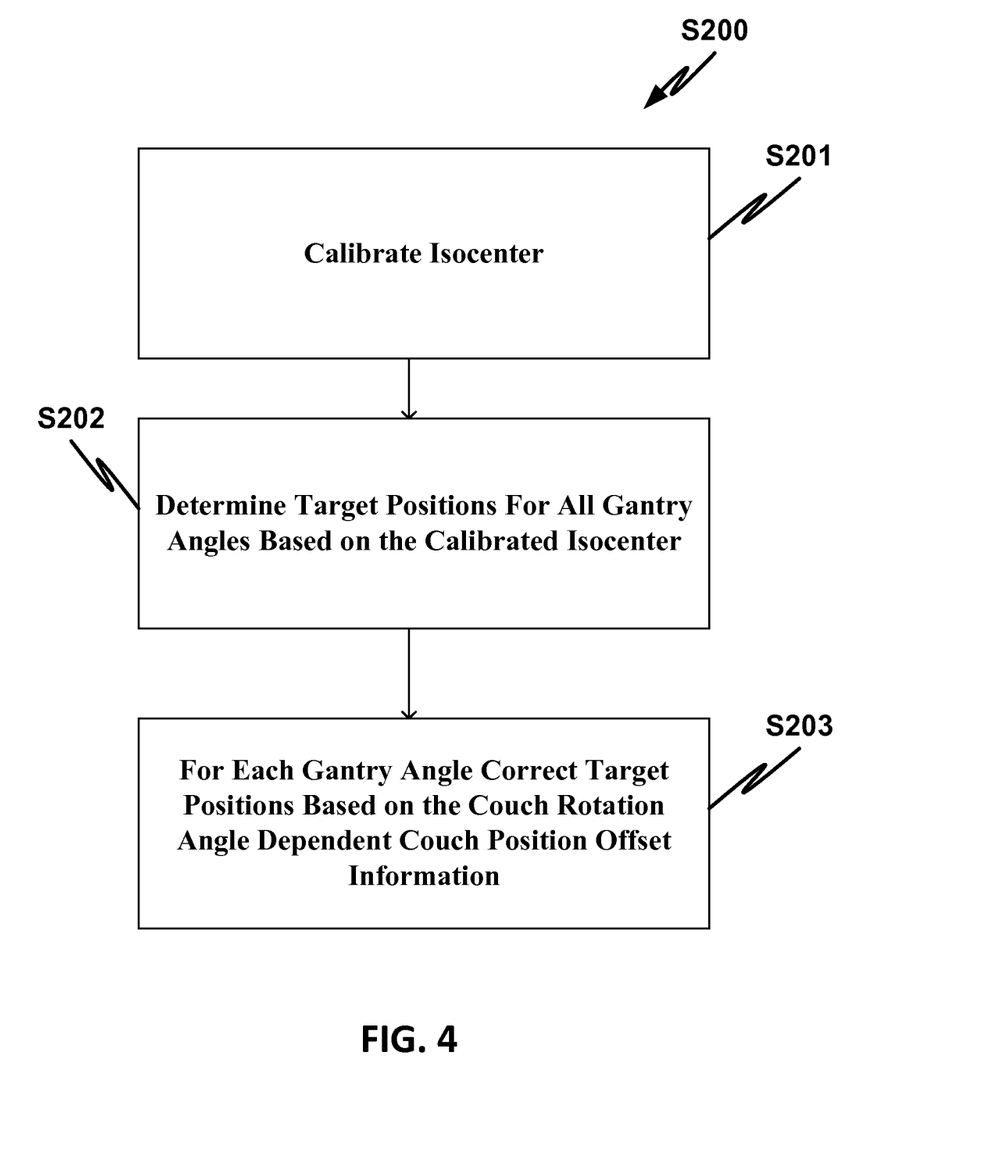
FIG. 4 illustrates an imaging-based calibration process according to one or more embodiments of the disclosed subject matter.

FIG. 4 illustrates a process S200 by which the treatment couch, and thus, a target, can be accurately positioned at the isocenter for each gantry angle, because the couch imperfections introduced by the couch rotation relative to the isocenter have been compensated for as shown herein. In step S201, the isocenter is calibrated based on the calibration offset information stored in Table 1. Once calibrated, the positions of the target relative to the isocenter for each gantry angle can be determined in S202. Then, in step S203, for each gantry angle, the determined target position can be corrected based on the couch rotation-angle dependent couch position offset information stored in Table 3. Additionally, target position can be further corrected by applying the couch rotation-angle dependent couch position offset information obtained for a particular weight of the patient as shown in Table 4, and thus correct for the sagging errors introduced by the weight of the patient.

Figure 5:
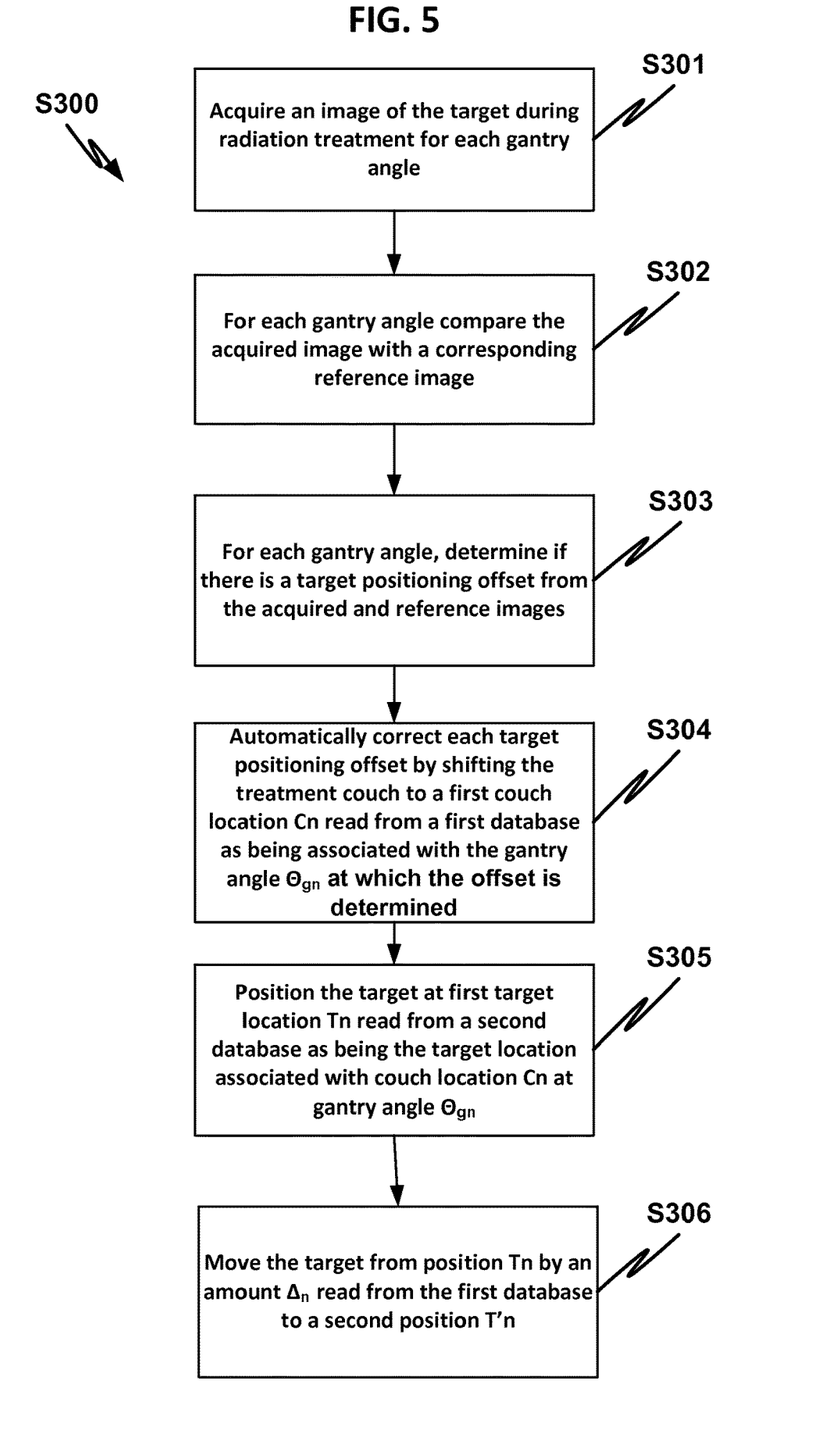
FIG. 5 illustrates an imaging-based automatic target positioning method according to one or more embodiments of the disclosed subject matter.

FIG. 5 illustrates a process S300 by which, during radiation treatment, the target can be accurately and automatically positioned at the isocenter for each gantry angle based on the parameters saved in Tables 1-3. As previously discussed, during treatment, a plurality of radiation beams are directed to the target area of interest from several positions outside the body. The gantry is rotated to provide the radiation beams from different positions. To aid the positioning of the patient, setup images are acquired from multiple gantry angles and the target position is determined from these images.

For each gantry angle, the images acquired during the radiation treatment session (S301) are compared in S302 with previously determined reference images of the target. When there is a difference between the acquired and reference images, it is determined that the target is offset from the desired location. A target positioning offset is thus determined in S303 for each gantry angle. These offsets are corrected in S304 by an operator initiated automatic couch shift from the treatment console room. In order to move the target to the correct location, for each gantry angle $\Theta_{gn}$ where a target offset is determined, the target is first moved (S305) to a first target location $T_n$, which was previously determined to be the isocenter for that particular gantry angle $\Theta_{gn}$ (S301), as shown in Table 1. The target is moved to target location $T_n$ by moving the couch 102 to location $C_n$, as shown in Table 3. In order to compensate for errors introduced by the couch movement, the target is then automatically repositioned in S306 to location $T'_n$, which represents the corrected target location. The corrected target location $T'_n$ represents the location of the target after it has been moved from the initial target location $T_n$ by an amount, which equals the couch rotation dependent offset value $\Delta_{cn}$ read from Table 3 corresponding to the rotation angle $\Theta c_n$ associated with the couch location $C_n$. The target location offsets are corrected in this way for every gantry angle where a target offset is detected.

Additionally, target position can be further corrected by applying the couch rotation-angle dependent couch position offset information obtained for a particular weight of the patient as shown in Table 4, and thus correct for the couch sagging errors introduced by the weight of the patient.

In yet another embodiment, the software program included in the software modules of controller 120 can also include an optimization module operable to optimize the treatment plan prior to and during treatment delivery. Optimization in real-time during treatment delivery can better take into account a variety of factors, such as patient anatomical and physiological changes (e.g., respiration and other movement, etc.), and machine configuration changes, including (e.g., beam output factors, couch error, collimator jaw and MLC imperfections and leaf errors, etc.). Real time modification of the beam intensity can account for these changes by re-optimize beamlets in real time. The optimization module can also account for cumulative errors and to adjust the treatment plan accordingly. As such, the software can further include offsets for the errors introduced by collimator jaw and MLC imperfections.

It is thus apparent that an imaging-based quality assurance system and protocol is disclosed for a radiation treatment device, comprising: performing an isocenter calibration process by using a target to calculate deviations between a treatment beam axis and an imaging beam axis at a plurality of gantry angles; for each gantry angle, determining a position of the target relative to the calibrated isocenter; generating couch rotation angle dependent couch position offset information by: acquiring a plurality of X-ray images of a calibration device positioned on the couch at different couch rotation angles; determining positions of the couch at all couch rotation angles based on the X-ray images; comparing each determined couch position with a reference couch position for each couch rotation angle; calculating couch position offsets between the determined and the reference couch positions for each couch rotation angle; and calibrating the position information of the target for each gantry angle using the couch rotation angle dependent couch position offset information.

It is further appreciated that the target position information can be further calibrated using a couch compensation protocol to compensate for couch load and position dependent mechanical deflections.

It is further to be appreciated that the system and method can further comprise determining offsets for collimator jaw or MLC imperfections, wherein the correcting of the target position includes correcting the target position by combining the gantry-angle dependent isocenter beam deviation information with the couch rotation-angle dependent couch position offset information, the load-dependent couch offset values, and the offsets for collimator jaw or MLC imperfections.

It is also to be appreciated that a method for automatically positioning a target at an isocenter for each gantry angle is disclosed, comprising: generating images of the target at a plurality of gantry angles; determining a target position for each gantry angle from the acquired images; for each gantry angle, determining a target location offset by comparing the acquired image for that gantry angle with a corresponding reference image; and correcting target location offset for each gantry angle by: moving the target to the isocenter; and correcting the target location by moving the target by a distance which equals a previously determined couch rotation dependent offset value. In embodiments, the method can further comprise generating load-dependent couch offset information by measuring errors included in the motion of the couch due to different loads positioned thereon. The method can also further comprise correcting target position by combining the couch rotation-angle dependent couch position offset information with the load-dependent couch offset information.

It will be appreciated that the processes, systems, and sections described above can be implemented in hardware, hardware programmed by software, software instruction stored on a non-transitory computer readable medium or a combination of the above. For example, a method for can be implemented using a processor configured to execute a sequence of programmed instructions stored on a non-transitory computer readable medium. The processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms.

Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized.

Embodiments of the method, system, and computer program product can be implemented in hardware and/or software using any known or later developed systems or structures, devices and/or software by those of ordinary skill in the applicable art from the function description provided herein and with a general basic knowledge of control systems, image processing and classification, and/or computer programming arts.

Moreover, embodiments of the disclosed method, system, and computer program product can be implemented in software executed on a programmed general purpose computer, a special purpose computer, a microprocessor, or the like.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, an imaging-based calibration system and method for radiation treatment couch position compensations. Many alternatives, modifications, and variations are Zo enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A non-transitory computer-readable storage medium upon which is embodied a sequence of programmed instructions, which when executed by a computer processing system, causes the computer processing system to perform a method for calibrating a radiation treatment system including a gantry and a treatment couch, the performing method including:
    generating gantry-angle dependent isocenter beam deviation information;
    generating couch rotation-angle dependent couch position offset information; and
    correcting a target position by combining the gantry-angle dependent isocenter beam deviation information with the couch rotation-angle dependent couch position offset information.

2. The non-transitory computer-readable storage medium of claim 1, wherein the generating of the gantry-angle dependent isocenter beam deviation information includes:
    acquiring X-ray images of a calibration device at a plurality of gantry angles;
    determining deviations of an isocenter for the plurality of gantry angles from the X-ray images; and
    determining a position of a target for each gantry angle of the plurality of gantry angles based on a corresponding deviation of the isocenter.

3. The non-transitory computer-readable storage medium of claim 1, wherein the generating of the couch rotation-angle dependent couch position offset information includes:
    acquiring a plurality of X-ray images of a calibration device positioned on the treatment couch by delivering X-rays from an X-ray source onto the calibration device, the treatment couch being rotated over a couch rotation range;
    determining positions of the calibration device at a plurality of couch rotation angles from corresponding X-ray images;
    translating each determined position of the calibration device to a an acquired couch location;
    comparing the acquired couch locations with corresponding reference couch locations; and
    calculating a couch position offset value for each couch rotation angle of the plurality of couch rotation angles based on a result of the comparing.

4. The non-transitory computer-readable storage medium of claim 3, wherein the method further includes determining the reference couch locations for the plurality of couch rotation angles using a camera-based system or a couch readout system, the couch readout system including a potentiometer, or an optical or magnetic angle or linear encoder.

5. The non-transitory computer-readable storage medium of claim 3, wherein the acquiring of the plurality of X-ray images of the calibration device position of the treatment couch includes:
    positioning the gantry including an X-ray source to a first position and rotating the treatment couch to its maximum rotation angle in a first direction while acquiring X-ray images of the calibration device at a plurality of couch rotation angles, then rotating the treatment couch to its maximum rotation angle in a second direction while acquiring X-ray images of the calibration device at a plurality of couch rotation angles; and positioning the gantry at a second position and rotating the treatment couch to its maximum rotation angle in the first direction while acquiring X-ray images of the calibration device at a plurality of couch rotation angles, then rotating the treatment couch to its maximum rotation angle in the second direction while acquiring X-ray images of the calibration device at a plurality of couch rotation angles.

6. The non-transitory computer-readable storage medium of claim 5, wherein the method further includes positioning the gantry at a third position and rotating the treatment couch to its maximum rotation angle in the first direction while acquiring X-ray images of the calibration device at a plurality of couch rotation angles, then rotating the treatment couch to its maximum rotation angle in the second direction while acquiring X-ray images of the calibration device at a plurality of couch rotation angles.

7. The non-transitory computer-readable storage medium of claim 6, wherein the gantry is configured to rotate through 360 degrees, and the first position of the gantry is being at 0 degree, the second position of the gantry being between 30-40 or between 5-60 degrees, and the third position of the gantry being between 320-340 or between 300-355 degrees.

8. The non-transitory computer-readable storage medium of claim 6, wherein the gantry is configured to rotate through 360 degrees, and the first position of the gantry angle being at 180 degrees, the second position of the gantry being between 210-220 or between 185-240 degrees, and the third position of the gantry being between 140-160 or between 120-175 degrees.

9. The non-transitory computer-readable storage medium of claim 3, wherein the method further includes positioning the calibration device or the treatment couch along a vertical axis at a height, which is at one of a height of the isocenter, above the isocenter, or below the isocenter, wherein the treatment couch is rotated in a first direction which is clockwise and in a second direction which is counterclockwise, wherein the plurality of couch rotation angles include 1 degree rotation angles, and wherein the couch rotation range includes an entire rotation range of the treatment couch.

10. The non-transitory computer-readable storage medium of claim 3, wherein the X-ray source is an MV X-ray source and the X-ray images are MV images, or the X-ray source is a kV source and the X-ray images are kV images.

11. The non-transitory computer-readable storage medium of claim 3, wherein the couch position offset values for each couch rotation angle include values for displacements of the treatment couch from the reference couch location in a longitudinal direction, a lateral direction, a vertical direction, and rotational directions, and wherein the rotational directions include rotations along a pitch axis and a roll axis.

12. The non-transitory computer-readable storage medium of claim 11, wherein the method further includes storing the couch rotation-angle dependent couch position offset values and the gantry-angle dependent isocenter beam deviation information in a tabular database.

13. The non-transitory computer-readable storage medium of claim 3, wherein the correcting of the target position includes positioning target at an isocenter for a particular gantry angle based on the gantry-angle dependent isocenter beam deviation information and repositioning of the target at the isocenter based on the couch rotation dependent couch position offset values.

14. The non-transitory computer-readable storage medium of claim 1, wherein the method further includes determining load-dependent couch offset values.

15. The non-transitory computer-readable storage medium of claim 14, wherein the method further includes correcting the target position by combining the gantry-angle dependent isocenter beam deviation information with the couch rotation-angle dependent couch position offset information and the load-dependent couch offset values.

16. The non-transitory computer-readable storage medium of claim 15, wherein the method further includes determining offsets for collimator jaw or MLC imperfections, wherein the correcting of the target position includes correcting the target position by combining the gantry-angle dependent isocenter beam deviation information with the couch rotation-angle dependent couch position offset information, the load-dependent couch offset values, and the offsets for collimator jaw or MLC imperfections.

17. A non-transitory computer-readable storage medium upon which is embodied a sequence of programmed instructions, which when executed by a computer processing system, causes the computer processing system to perform an imaging-based quality assurance protocol for a radiation treatment device, the imaging-based quality assurance protocol comprising:

determining a calibrated isocenter of the radiation treatment device by performing an isocenter calibration process by using a target to calculate deviations between a treatment beam axis and an imaging beam axis at a plurality of gantry angles;

for each gantry angle, determining a position of the target relative to the calibrated isocenter;

generating couch rotation-angle dependent couch position offset information by:
positioning a calibration device on a couch;
acquiring a plurality of X-ray images of the calibration device at different couch rotation angles;
determining positions of the couch at all couch rotation angles based on the plurality of X-ray images;
comparing each determined couch position with a reference couch position for each couch rotation angle; and
calculating couch position offsets between the determined positions of the couch and corresponding reference couch positions for each couch rotation angle; and calibrating position information of the target for each gantry angle using the couch rotation-angle dependent couch position offset information.

18. The non-transitory computer-readable storage medium of claim 17, wherein the calibrating the position information of the target for each gantry angle further includes using a couch compensation protocol to compensate for couch load and position dependent mechanical deflections.

19. The non-transitory computer-readable storage medium of claim 18, wherein the imaging-based quality assurance protocol further includes storing the couch compensation protocol in an internal readout system.

20. The non-transitory computer-readable storage medium of claim 19, wherein the imaging-based quality assurance protocol further includes determining offsets for collimator jaw or MLC imperfections, wherein the calibrating the position information of the target for each gantry angle further includes combining the gantry-angle dependent isocenter beam deviation information with the couch rotation-angle dependent couch position offset information, offset values for couch load, and offset values for collimator jaw or MLC imperfections.

\* \* \* \* \*